United States Patent
Ikenaka et al.

(10) Patent No.: US 12,099,070 B2
(45) Date of Patent: Sep. 24, 2024

(54) METHOD AND KIT FOR DISCRIMINATING BETWEEN PARKINSON'S DISEASE AND MULTIPLE SYSTEM ATROPHY

(71) Applicant: Osaka University, Osaka (JP)

(72) Inventors: Kensuke Ikenaka, Osaka (JP); Hideki Mochizuki, Osaka (JP); Cesar Aguirre Martinez, Osaka (JP); Yuji Goto, Osaka (JP); Masatomo So, Osaka (JP); Keita Kakuda, Osaka (JP); Hirotsugu Ogi, Osaka (JP); Kentaro Noi, Osaka (JP)

(73) Assignee: Osaka University, Osaka (JP)

( * ) Notice: Subject to any disclaimer, the term of this patent is extended or adjusted under 35 U.S.C. 154(b) by 406 days.

(21) Appl. No.: 17/425,197

(22) PCT Filed: Feb. 3, 2020

(86) PCT No.: PCT/JP2020/003900
§ 371 (c)(1),
(2) Date: Jul. 22, 2021

(87) PCT Pub. No.: WO2020/162388
PCT Pub. Date: Aug. 13, 2020

(65) Prior Publication Data
US 2022/0128576 A1  Apr. 28, 2022

(30) Foreign Application Priority Data
Feb. 5, 2019  (JP) .................... 2019-018811

(51) Int. Cl.
*G01N 33/68*  (2006.01)
*G01N 33/58*  (2006.01)

(52) U.S. Cl.
CPC ....... *G01N 33/6896* (2013.01); *G01N 33/582* (2013.01); *G01N 33/6845* (2013.01); *G01N 2333/47* (2013.01); *G01N 2800/2835* (2013.01)

(58) Field of Classification Search
CPC ............. G01N 33/6896; G01N 33/582; G01N 33/6845; G01N 2333/47; G01N 2800/2835
(Continued)

(56) References Cited

U.S. PATENT DOCUMENTS

2019/0277863 A1  9/2019  Barbour
2019/0302128 A1  10/2019  Green et al.

FOREIGN PATENT DOCUMENTS

JP        2018-91844 A     6/2018
WO    WO 2016/040905 A1   3/2016
(Continued)

OTHER PUBLICATIONS

Groveman BR, et al. Rapid and ultra-sensitive quantitation of disease-associated α-synuclein seeds in brain and cerebrospinal fluid by αSyn RT-QuIC. Acta Neuropathol Commun. Feb. 9, 2018;6(1):7 (Year: 2018).*

(Continued)

*Primary Examiner* — Christopher L Chin
*Assistant Examiner* — Christina Lusi
(74) *Attorney, Agent, or Firm* — Knobbe, Martens, Olson & Bear, LLP (57) ABSTRACT

A method for discriminating between Parkinson's disease and multiple system atrophy, the method comprising the steps of: (1) preparing a solution containing α-synuclein monomers having a tendency to produce rod-like aggregates and/or a solution containing α-synuclein monomers having a tendency to produce twisted aggregates; (2) adding a (Continued)

biological sample from a subject to the solution(s) containing the α-synuclein monomers prepared in step (1); (3) allowing the α-synuclein monomers to aggregate in the solution(s) obtained in step (2); and (4) detecting α-synuclein aggregates formed in step (3).

6 Claims, 7 Drawing Sheets

Specification includes a Sequence Listing.

(58) Field of Classification Search
USPC .............................. 435/7.1, 7.92; 436/501, 86
See application file for complete search history.

(56) References Cited

FOREIGN PATENT DOCUMENTS

| WO | WO 2018/007817 A1 | 1/2018 | |
|----|-------------------|--------|---|
| WO | WO 2018/102763 A1 | 6/2018 | |
| WO | WO-2019070480 A1 * | 4/2019 | ........... G01N 33/543 |

OTHER PUBLICATIONS

Strohaker, T. (2019) Structural characterization of alpha synuclein aggregates seeded by patient material. Doctoral Thesis, Georg-August-Universität Göttingen. (Year: 2019).*

Ariesandi et al. Temperature-dependent structural changes of Parkinson's alpha-synuclein reveal the role of pre-existing oligomers in alpha-synuclein fibrillization. PLoS One. 2013;8(1):e53487. (Year: 2013).*

Atarashi, Ryuichiro et al., "Ultrasensitive human prion detection in cerebrospinal fluid by real-time quaking-induced conversion" Nature Medicine, Feb. 2011, pp. 175-178, vol. 17, No. 2.

De Luca, Chiara Maria Giulia et al., "Efficient RT-QuIC seeding activity for α-synuclein in olfactory mucosa samples of patients with Parkinson's disease and multiple system atrophy" Translational Neurodegeneration, 2019, pp. 1-14, vol. 8, No. 24.

Fairfoul, Graham et al., "Alpha-synuclein RT-QuIC in the CSF of patients with alpha-synucleinopathies" Annals of Clinical and Translational Neurology, 2016, pp. 812-818, vol. 3, No. 10.

Li, Binsen et al., "Cryo-EM of full-length α-synuclein reveals fibril polymorphs with a common structural kernel" Nature Communications, 2018, pp. 1-10, vol. 9, No. 1.

Peng, Chao et al., "Cellular milieu imparts distinct pathological α-synuclein strains in α—synucleinopathies" Nature, May 2018, pp. 558-563, vol. 557.

Shahnawaz, Mohammad et al., "Development of a Biochemical Diagnosis of Parkinson Disease by Detection of α-Synuclein Misfolded Aggregates in Cerebrospinal Fluid" JAMA Neurology, 2017, pp. 163-172, vol. 74, No. 2.

Tokuda, T. et al., "Detection of elevated levels of α-synuclein oligomers in CSF from patients with Parkinson disease" Neurology, 2010, pp. 1766-1772, vol. 75.

International Search Report for PCT/JP2020/003900 dated Mar. 24, 2020.

International Preliminary Report on Patentability in corresponding International Application No. PCT/JP2020/003900.

Office Action for JP 2020-571177 issued Jul. 26, 2022.

Spillantini, Maria Grazia et al., "Filamentous α-synuclein inclusions link multiple system atrophy with Parkinson's disease and dementia with Lewy bodies" Neuroscience Letters, 1998, pp. 205-208, vol. 251.

Spillantini, Maria Grazia et al., "α-Synuclein in filamentous inclusions of Lewy bodies from Parkinson's disease and dementia with Lewy bodies" Proc. Nat. Acad. Sci., May 1998, pp. 6469-6473, vol. 95.

Supplementary European Search Report for EP 20752099 dated Mar. 10, 2022.

Office Action for JP 2020-571177 dated Mar. 29, 2022.

* cited by examiner

METHOD AND KIT FOR DISCRIMINATING BETWEEN PARKINSON'S DISEASE AND MULTIPLE SYSTEM ATROPHY

CROSS REFERENCE TO RELATED APPLICATIONS

This application is a U.S. National Phase Application of PCT International Application Number PCT/JP2020/003900, filed on Feb. 3, 2020, designating the United States of America and published in the Japanese language, which is an International Application of and claims the benefit of priority to Japanese Patent Application No. 2019-018811, filed on Feb. 5, 2019. The disclosures of the above-referenced applications are hereby expressly incorporated by reference in their entireties.

REFERENCE TO SEQUENCE LISTING

A Sequence Listing submitted as an ASCII text file via EFS-Web is hereby incorporated by reference in accordance with 37 U.S.C. § 1.52(e). The name of the ASCII text file for the Sequence Listing is SeqList-IWAT007-014APC.txt, the date of creation of the ASCII text file is Jan. 23, 2020, and the size of the ASCII text file is 6 KB.

TECHNICAL FIELD

The present invention relates to a method and a kit for discriminating between Parkinson's disease and multiple system atrophy.

BACKGROUND ART

Parkinson's disease (may be abbreviated as PD) and multiple system atrophy (may be abbreviated as MSA) cause aggregation and accumulation of α-synuclein in the brain, and lead to neuron death. Some of α-synuclein aggregates leak into the cerebrospinal fluid, and such α-synuclein aggregates can be quantified and advantageously utilized for diagnosis of PD and MSA. To achieve this concept, two major methods have been developed.

The first one is ELISA for the detection of only α-synuclein aggregates (non-patent literature 1). PD patients and control patients were compared by this method, and the results revealed that the levels of α-synuclein aggregates in the PD patients were elevated as compared with the control patients. The second major method is called RT-QUIC or PMCA assay (non-patent literature 2). This method is based on the principle that a small amount of α-synuclein aggregates present in a sample can be amplified by mixing the sample with recombinant α-synuclein monomers purified after expression in *Escherichia coli* and then subjecting the mixture to stimuli such as shaking and/or ultrasonication. Thioflavin T (may be abbreviated as ThT) is added to the system, which is a compound that emits fluorescence upon binding to α-synuclein fibrillar aggregates. The fluorescence increases as more aggregates are formed, and it is measured to determine the extent of the aggregation reaction. The larger is the amount of α-synuclein aggregates contained in a sample, the much more faster will increase the fluorescence of ThT. Based on this relationship, the amount of α-synuclein aggregates contained in the initial sample can be estimated. This method has revealed that a larger amount of α-synuclein aggregates are present in the cerebrospinal fluid of PD and MSA patients as compared with control patients (non-patent literatures 3 and 4).

The above reports indicate that the aggregation curves of α-synuclein in PD and MSA patients are equally increased, which renders it impossible to discriminate between both diseases. However, discrimination between PD and MSA at the early stage of the onset is very important to determine the treatment strategy for the patients, predicting the prognosis, and conducting clinical trials for these diseases, for which fundamental therapeutics have not been developed yet. To achieve these goals, there is a very great need for development of methods and kits capable of discriminating between PD and MSA and of reflecting the background of pathological conditions.

CITATION LIST

Patent Literature

Non-patent literature 1: Tokuda et al. Neurology. 2010 Nov. 16; 75(20):1766-1772.
Non-patent literature 2: Atarashi R et al. Nat Med. 2011 February; 17(2):175-178.
Non-patent literature 3: Shahnawaz M et al. JAMA Neurol. 2017 Feb. 1; 74(2); 163-172.
Non-patent literature 4: Fairfoul et al. Ann Clin Transl Neurol, 2016 Aug. 28; 3(10).

SUMMARY OF INVENTION

Technical Problem

An object of the present invention is to provide a method for discriminating between Parkinson's disease and multiple system atrophy. Another object of the present invention is to provide a kit for discriminating between Parkinson's disease and multiple system atrophy.

Solution to Problem

The present invention was made to solve the above problems and includes the following.
[1] A method for discriminating between Parkinson's disease and multiple system atrophy, the method comprising the steps of:
 (1) preparing a solution containing α-synuclein monomers having a tendency to produce rod-like aggregates and/or a solution containing α-synuclein monomers having a tendency to produce twisted aggregates;
 (2) adding a biological sample from a subject to the solution(s) containing the α-synuclein monomers prepared in step (1);
 (3) allowing the α-synuclein monomers to aggregate in the solution(s) obtained in step (2); and
 (4) detecting α-synuclein aggregates formed in step (3).
[2] A method for supporting diagnosis of Parkinson's disease or multiple system atrophy, the method comprising the steps of:
 (1) preparing a solution containing α-synuclein monomers having a tendency to produce rod-like aggregates and/or a solution containing α-synuclein monomers having a tendency to produce twisted aggregates;
 (2) adding a biological sample from a subject to the solution(s) containing the α-synuclein monomers prepared in step (1);
 (3) allowing the α-synuclein monomers to aggregate in the solution(s) obtained in step (2); and
 (4) detecting α-synuclein aggregates formed in step (3).

[3] The method according to the above [1] or [2], wherein the α-synuclein consists of an amino acid sequence having 95% or more identity to the amino acid sequence of SEQ ID NO: 1.

[4] The method according to the above [3], wherein the α-synuclein monomers having a tendency to produce rod-like aggregates are α-synuclein monomers that are present in a fraction passing through an ultrafiltration membrane filter with a molecular weight cut-off of 30 kDa, and the α-synuclein monomers having a tendency to produce twisted aggregates are α-synuclein monomers that are present in a fraction not passing through an ultrafiltration membrane filter with a molecular weight cut-off of 30 kDa.

[5] The method according to the above [1] or [2], wherein after addition of the biological sample from the subject to the solution containing the α-synuclein monomers having a tendency to produce rod-like aggregates, step (3) is initiated simultaneously both in the solution and in a control not containing the biological sample, and wherein when amplification of α-synuclein aggregates in the solution containing the biological sample is more rapid than that in the control, the subject is determined to suffer from Parkinson's disease.

[6] The method according to the above [1] or [2], wherein after addition of the biological sample from the subject to both of the solution containing the α-synuclein monomers having a tendency to produce rod-like aggregates and the solution containing the α-synuclein monomers having a tendency to produce twisted aggregates, step (3) is initiated simultaneously in both solutions, and wherein when amplification of α-synuclein aggregates in the solution containing the α-synuclein monomers having a tendency to produce rod-like aggregates is more rapid than that in the solution containing the α-synuclein monomers having a tendency to produce twisted aggregates, the subject is determined to suffer from Parkinson's disease.

[7] The method according to the above [5] or [6], wherein when the α-synuclein aggregates amplified after addition of the biological sample from the subject to the solution containing the α-synuclein monomers having a tendency to produce rod-like aggregates are rod-like aggregates, the subject is determined to suffer from Parkinson's disease.

[8] The method according to the above [1] or [2], wherein after addition of the biological sample from the subject to the solution containing the α-synuclein monomers having a tendency to produce twisted aggregates, step (3) is initiated simultaneously both in the solution and in a control not containing the biological sample, and wherein when amplification of α-synuclein aggregates in the solution containing the biological sample is more rapid than that in the control, the subject is determined to suffer from multiple system atrophy.

[9] The method according to the above [1] or [2], wherein after addition of the biological sample from the subject simultaneously to both of the solution containing the α-synuclein monomers having a tendency to produce rod-like aggregates and the solution containing the α-synuclein monomers having a tendency to produce twisted aggregates, step (3) is initiated simultaneously in both solutions, and wherein when amplification of α-synuclein aggregates in the solution containing the α-synuclein monomers having a tendency to produce twisted aggregates is more rapid than that in the solution containing the α-synuclein monomers having a tendency to produce rod-like aggregates, the subject is determined to suffer from multiple system atrophy.

[10] The method according to the above [1] or [2], wherein when both of the α-synuclein aggregates formed after addition of the biological sample from the subject to the solution containing the α-synuclein monomers having a tendency to produce rod-like aggregates and the α-synuclein aggregates formed after addition of the biological sample from the subject to the solution containing the α-synuclein monomers having a tendency to produce twisted aggregates are twisted aggregates of α-synuclein, the subject is determined to suffer from multiple system atrophy.

[11] A kit for discriminating between Parkinson's disease and multiple system atrophy or for supporting diagnosis of Parkinson's disease or multiple system atrophy, the kit comprising α-synuclein monomers having a tendency to produce rod-like aggregates and/or α-synuclein monomers having a tendency to produce twisted aggregates.

Advantageous Effects of Invention

The present invention can be used to discriminate between Parkinson's disease and multiple system atrophy in an easy and convenient manner. The method of the present invention is very useful for discriminating between these diseases at a very early stage.

BRIEF DESCRIPTION OF DRAWINGS

FIG. 1 shows a graph of the results of size-exclusion chromatography (SEC) of purified recombinant wild-type human α-synuclein produced by *Escherichia coli* and passed through different types of filters. FIG. 1 also shows an image of native PAGE of the fractions of the two peaks (the low-molecular-weight fraction (LMW-syn) and the high-molecular-weight fraction (HMW-syn)) observed in SEC.

FIG. 2 shows graphs of the emission fluorescence intensity measured over time in an LMW-syn solution and a HMW-syn solution after addition of thioflavin T (ThT) followed by intermittent ultrasonication (alternating cycles of 1-minute ultrasonication and 9-minute resting) for 24 hours. FIG. 2 also shows transmission electron microscope images of aggregates formed after 24 hours of ultrasonication.

DESCRIPTION OF EMBODIMENTS

Discriminating Method and Diagnosis Supporting Method

The present invention provides a method for discriminating between Parkinson's disease and multiple system atrophy or for supporting discrimination between these diseases. The present invention also provides a method for supporting diagnosis of Parkinson's disease or multiple system atrophy. The present invention can be used to help a physician discriminate between Parkinson's disease and multiple system atrophy and/or diagnose these diseases. The present invention is useful for supporting diagnosis of and discrimination between Parkinson's disease and multiple system atrophy in patients even when correct clinical differentiation and diagnosis of these diseases are difficult, e.g., before or immediately after the onset of the diseases.

The method of the present invention comprises the following steps (1) to (4):

(1) preparing a solution containing α-synuclein monomers having a tendency to produce rod-like aggregates and/or a solution containing α-synuclein monomers having a tendency to produce twisted aggregates;

(2) adding a biological sample from a subject to the solution(s) containing the α-synuclein monomers prepared in step (1);

(3) allowing the α-synuclein monomers to aggregate in the solution(s) obtained in step (2); and (4) detecting α-synuclein aggregates formed in step (3).

The α-synuclein used in the present invention may be purified, naturally occurring α-synuclein, or recombinant α-synuclein produced by gene engineering. The α-synuclein may be from any organisms, and may be α-synuclein from a mammal, α-synuclein from a primate, or α-synuclein from a human.

A suitable α-synuclein for use in the present invention is α-synuclein consisting of the amino acid sequence of SEQ ID NO: 1. The amino acid sequence of SEQ ID NO: 1 is a wild-type amino acid sequence of human α-synuclein, and is deposited in known databases, such as NCBI, under Accession No. NP_000336. The α-synuclein used in the present invention may consist of an amino acid sequence having 90% or more identity, 91% or more identity, 92% or more identity, 93% or more identity, 94% or more identity, 95% or more identity, 96% or more identity, 97% or more identity, 98% or more identity, or 99% or more identity to the amino acid sequence of SEQ ID NO: 1. The α-synuclein used in the present invention preferably consists of an amino acid sequence having 95% or more identity to the amino acid sequence of SEQ ID NO: 1. Examples of such α-synuclein include wild-type mouse α-synuclein with the amino acid sequence of SEQ ID NO: 2 (the amino acid sequence under Accession No. NP_033247), wild-type rat α-synuclein with the amino acid sequence of SEQ ID NO: 3 (the amino acid sequence under Accession No. NP_062042), and wild-type marmoset (common marmoset, *Callithrix jacchus*) α-synuclein with the amino acid sequence of SEQ ID NO: 4 (the amino acid sequence under Accession No. XP 008991227).

The α-synuclein used in the present invention may be α-synuclein consisting of the amino acid sequence of SEQ ID NO: 1 having a mutation. Such α-synuclein may consist of the amino acid sequence of SEQ ID NO: 1 having deletion, substitution or addition of 1, 2, 3, 4, 5, 6, 7, 8, 9, 10, 11, 12, 13, or 14 amino acids.

Recombinant α-synuclein used in the present invention can be produced using a known genetic engineering technique as appropriate. Specifically, a DNA encoding the amino acid sequence of SEQ ID NO: 1 (for example, a DNA containing the coding sequence (CDS) of the nucleotide sequence of Accession No. NM_000345) is inserted into a known expression vector. The resulting expression vector is introduced into appropriate host cells for the expression of recombinant α-synuclein. The expressed α-synuclein is purified by a known purification method. The host cells may be any types of host cells that are conventionally used for expression of proteins, and examples thereof may include, but are not limited to, *Escherichia coli, Bacillus subtilis*, yeasts, plant cells, and animal cells.

The recombinant α-synuclein may be tagged with an affinity tag to facilitate purification. Examples of such a tag include FLAG tag, histidine tag, c-Myc tag, HA tag, AU1 tag, GST tag, MBP tag, fluorescence protein tags (for example, GFP, YFP, RFP, CFP, BFP, etc.), and immunoglobulin Fc tag. Such a tag sequence may be attached to the N- or C-terminus of the α-synuclein polypeptide. The recombinant α-synuclein tagged with an affinity tag may be used in the present invention without removal of the affinity tag, or may be used in the present invention after cleavage of the affinity tag.

The present invention employs α-synuclein monomers. Whether α-synuclein is in the form of a monomer can be determined by, for example, detecting a single band at a molecular weight corresponding to that of α-synuclein monomers in native PAGE, or measuring the molecular weight by mass spectroscopy, or performing analytical ultracentrifugation.

The term "α-synuclein monomers having a tendency to produce rod-like aggregates" (hereinafter may be referred to as "rod-like aggregate-producing monomers") refers to α-synuclein monomers that tend to produce rod-like aggregates when aggregation is induced by ultrasonication or shaking in a solution containing the monomers without addition of aggregation-inducing aggregates (so-called seeds). The rod-like aggregates are characterized by aggregates having a straight shape without twisting as visually observed with a transmission electron microscope.

The term "α-synuclein monomers having a tendency to produce twisted aggregates" (hereinafter may be referred to as "twisted aggregate-producing monomers") refers to α-synuclein monomers that tend to produce twisted aggregates when aggregation is induced by ultrasonication or shaking in a solution containing the monomers without addition of aggregation-inducing aggregates (so-called seeds). The twisted aggregates are characterized by aggregates having a twisted shape as visually observed with a transmission electron microscope. The twisted aggregates may be visible as a periodic color change between black and white by negative staining.

A buffer solution is used to prepare the solution(s) containing the α-synuclein monomers in step (1). Any buffer solution that can maintain the pH within a certain range can be used in the invention. The buffer solution may be selected from various types of buffer solutions (for example, phosphate buffer solution, phosphate buffered saline, Tris-hydrochloric acid buffer solution, Tris buffered saline, borate buffer solution, citrate buffer solution, acetate buffer solution, etc.). The buffer solution may be HEPPSO (N-(2-hydroxyethyl)piperazine-N'-(2-hydroxypropanesulfonic acid)), POPSO (piperazine-1,4-bis(2-hydroxypropanesulfonic acid) anhydride), HEPES (4-(2-hydroxyethyl)piperazine-1-ethanesulfonic acid), HEPPS (EPPS) (4-(2-hydroxyethyl)piperazine-1-propanesulfonic acid), TES (N-[tris(hydroxymethyl)methyl]-2-aminoethanesulfonic acid), or a combination thereof. A preferred buffer solution is HEPES. The pH of the buffer solution may be from 6.5 to 8.5, from 7.0 to 8.0, from 7.2 to 7.8, from 7.3 to 7.7, from 7.4 to 7.6, or from 7.4 to 7.5.

The buffer solution may contain a salt. Examples of the salt include sodium chloride, magnesium chloride, calcium chloride, potassium chloride, aluminium chloride, lithium chloride, strontium chloride, cobalt chloride, zinc chloride, iron chloride, copper chloride, magnesium sulfate, sodium sulfate, magnesium sulfate, ammonium sulfate, magnesium nitrate, sodium nitrate, magnesium nitrate, ammonium nitrate, sodium carbonate, magnesium carbonate, sodium hydrogen carbonate, disodium hydrogen phosphate, and calcium lactate. The concentration of the salt in the buffer solution may be from 0.001 mM to 1 M, from 0.1 mM to 800 mM, from 1 mM to 600 mM, from 10 mM to 500 mM, from 100 mM to 500 mM, from 200 mM to 400 mM, or from 250 mM to 350 mM.

The concentration of the α-synuclein monomers in the solution(s) containing the α-synuclein monomers may be, but is not limited to, from 0.01 mg/ml to 10 mg/ml, from 0.1 mg/ml to 1 mg/ml, from 0.2 mg/ml to 0.8 mg/ml, from 0.3 mg/ml to 0.7 mg/ml, from 0.4 mg/ml to 0.6 mg/ml, or at 0.5 mg/ml.

The biological sample to be added to the solution(s) containing the α-synuclein monomers in step (2) may be any sample that can be collected from a living body. Suitable biological samples may include, for example, brain tissue, skin tissue, cerebrospinal fluid, blood, urine, saliva, feces, etc. When the sample is prepared from a tissue, the sample is preferably a homogenate sample prepared by, for example, disrupting the tissue in an appropriate buffer solution. When the sample is a blood sample, the blood sample may be whole blood, plasma, serum, or the cell components of the blood (erythrocytes, leukocytes, platelets, etc.). The biological sample is collected from a subject. The subject subjected to the method of the present invention is preferably those who are suspected of suffering from Parkinson's disease or multiple system atrophy.

Mixing of the biological sample with the α-synuclein monomers may be performed in any container. Examples of the container may include flasks, dishes, petri dishes, multi-dishes, microplates, microwell plates, multi-plates, multi-well plates (6-, 12-, 24-, 48-, or 96-well multi-well plates), petri plates, tubes and trays.

The amount of the biological sample to be added to the solution(s) may be selected as appropriate for the biological sample used. For example, preliminary experiments may be performed to determine the optimum amount of the biological sample to be added to the solution(s). Alternatively, a series of sequential dilutions of the biological sample in an appropriate buffer solution may be used. When the biological sample is cerebrospinal fluid, the initial concentration of the cerebrospinal fluid may be from 0.1 (v/v) % to 10 (v/v) %, from 0.5 (v/v) % to 9 (v/v) %, from 1 (v/v) % to 8 (v/v) %, from 2 (v/v) % to 7 (v/v) %, from 3 (v/v) % to 6 (v/v) %, or from 4 (v/v) % to 5 (v/v) %.

Step (3) is performed by incubating the solution(s) of the α-synuclein monomers to which a biological sample from a subject has been added. As a control, only the solution(s) of the α-synuclein monomers may be incubated without addition of a biological sample from a subject in step (3). The incubation temperature is usually from 30° C. to 45° C., and may be from 32° C. to 42° C., from 34° C. to 40° C., from 36° C. to 38° C., or at 37° C.

The reaction mixture may be shaken during the incubation. The shaking may be performed with, for example, a shaking incubator. The shaking speed may be, but is not limited to, for example, from 200 rpm to 1,200 rpm, from 300 rpm to 800 rpm, from 400 rpm to 500 rpm, or from 420 rpm to 480 rpm.

Ultrasonication may be applied to the reaction mixture during the incubation. The ultrasonication may be performed with, for example, an ultrasonic homogenizer, an ultrasonic bath, etc., that are commercially available.

The aggregation reaction of α-synuclein in step (3) may be performed with alternating cycles of shaking or ultrasonication and resting. The shaking may be performed in alternating cycles of 30-second shaking and 30-second resting; 45-second shaking and 45-second resting; 60-second shaking and 60-second resting; or 70-second shaking and 70-second resting. The ultrasonication may be performed in alternating cycles of ultrasonication for 10 seconds to 3 minutes and resting for 30 seconds to 15 minutes; ultrasonication for 30 seconds to 2 minutes and resting for 1 minute to 12 minutes; ultrasonication for 45 seconds to 1 minute and 30 seconds and resting for 3 minutes to 20 minutes; or ultrasonication for 1 minute and resting for 9 minutes.

The duration required for accomplishing step (3) may be any length of time sufficient to allow formation of detectable aggregates. The duration of step (3) may be 24 hours or less, 20 hours or less, 15 hours or less, or 12 hours or less. The duration of step (3) may also be 3 hours or more, 5 hours or more, 7 hours or more, or 9 hours or more.

The detection of the α-synuclein aggregates in step (4) may be done by any method, and the detection method may be selected as appropriate from known detection methods of α-synuclein aggregates. Specific examples of such detection methods include enzyme immunoassay (EIA), immunochromatographic assay, latex agglutination method, radioimmunoassay (RIA), fluoroimmunoassay (FIA), luminescence immunoassay, surface plasmon resonance (SPR), Western blotting, electronmicroscopy, fluorescence microscopy, and fluorescence spectrometry. Fluorescence spectrometry is particularly suitable for the invention due to its ease of handling and shorter time to results.

When fluorescence spectrometry is used to detect the α-synuclein aggregates, a fluorescent dye that binds to amyloid fibrils and emits fluorescence is added to the reaction mixture containing the biological sample and the α-synuclein monomers in step (3). The fluorescent dye binds to the formed aggregates and emits fluorescence. The reaction mixture is then exposed to excitation light at an appropriate wavelength to excite the fluorescence of the dye, which is detected with a spectrometer, etc. The aggregates can be quantified by measuring the fluorescence intensity, and based on the quantification of the aggregates, the amount of the aggregates contained in the biological sample can be estimated. Examples of the fluorescent dye that binds to amyloid fibrils and emits fluorescence include thioflavin T (ThT), 1-bromo-2,5-bis(3-carboxy-4-hydroxystyryl)benzene, 1-fluoro-2,5-bis(3-carboxy-4-hydroxystyryl)benzene, and ProteoStat (registered trademark) amyloid detection reagent.

Detection of the α-synuclein aggregates in step (4) may be performed while allowing the formation of the aggregates to proceed in step (3), or the α-synuclein aggregates may be detected at multiple times in an intermittent manner. For example, the α-synuclein aggregates may be detected during the resting periods of alternating cycles of shaking or ultrasonication and resting. Detection of the α-synuclein aggregates may be performed for every cycle or once every two to five cycles, or at irregular intervals.

As demonstrated herein, the method of the present invention performed using the cerebrospinal fluid from a PD patient as a biological sample yields the following results (see Example 1 (5)).

(P1) When two aggregation reactions are simultaneously initiated in a solution containing the rod-like aggregate-producing monomers where one is with addition of the cerebrospinal fluid from a PD patient and the other is without addition of the cerebrospinal fluid from the PD patient (control), amplification of α-synuclein aggregates is more rapid in the solution containing the cerebrospinal fluid from the PD patient than that in the control.

(P2) When two aggregation reactions are simultaneously initiated where one is in a solution containing the rod-like aggregate-producing monomers with addition of the cerebrospinal fluid from a PD patient and the other is in a solution containing the twisted aggregate-producing monomers with addition of the cerebrospinal fluid from the PD patient, amplification of α-synuclein aggregates is more rapid in the solution containing the rod-like aggregate-producing monomers than that in the solution containing the twisted aggregate-producing monomers.

Therefore, when a biological sample from a subject subjected to the method of the present invention yields the results (P1) and/or (P2) as described above, the subject is determined to suffer from PD or be highly likely to suffer from PD. To ensure the determination of PD, the α-synuclein aggregates formed after addition of the biological sample from the subject to the solution containing the rod-like aggregate-producing monomers may be observed with an electron microscope to confirm that the α-synuclein aggregates are rod-like aggregates. Further, the α-synuclein aggregates formed after addition of the biological sample from the subject to the solution containing the twisted aggregate-producing monomers may be observed with an electron microscope to confirm that the α-synuclein aggregates are twisted aggregates.

Preferably, the subject is determined to suffer from PD or be highly likely to suffer from PD upon the satisfaction of all of the following conditions: the results (P1) and (P2) as described above are obtained; the α-synuclein aggregates formed after addition of a biological sample from the subject to a solution containing the rod-like aggregate-producing monomers are rod-like aggregates; and the α-synuclein aggregates formed after addition of a biological sample from the subject to a solution containing the twisted aggregate-producing monomers are twisted aggregates.

As demonstrated herein, the method of the present invention performed using the cerebrospinal fluid from a MSA patient as a biological sample yields the following results (see Example 1 (5)).

(M1) When two aggregation reactions are simultaneously initiated in a solution containing the twisted aggregate-producing monomers where one is with addition of the cerebrospinal fluid from a MSA patient and the other is without addition of the cerebrospinal fluid from the MSA patient (control), amplification of α-synuclein aggregates is more rapid in the solution containing the cerebrospinal fluid from the MSA patient than that in the control.

(M2) When two aggregation reactions are simultaneously initiated where one is in a solution containing the rod-like aggregate-producing monomers with addition of the cerebrospinal fluid from a MSA patient and the other is in a solution containing the twisted aggregate-producing monomers with addition of the cerebrospinal fluid from the MSA patient, amplification of α-synuclein aggregates is more rapid in the solution containing the twisted aggregate-producing monomers than that in the solution containing the rod-like aggregate-producing monomers.

(M3) Both of α-synuclein aggregates formed after addition of the cerebrospinal fluid from a MSA patient to a solution containing the rod-like aggregate-producing monomers and α-synuclein aggregates formed after addition of the cerebrospinal fluid from the MSA patient to a solution containing the twisted aggregate-producing monomers are twisted aggregates.

Therefore, when a biological sample from a subject subjected to the method of the present invention yields any one or more of the results (M1), (M2) and (M3) as described above, the subject is determined to suffer from MSA or be highly likely to suffer from MSA. More preferably, the subject is determined to suffer from MSA or be highly likely to suffer from MSA when two or more of the results (M1), (M2) and (M3) are obtained. Further preferably, the subject is determined to suffer from MSA or be highly likely to suffer from MSA when all of the results (M1), (M2) and (M3) are obtained.

When a biological sample from a subject subjected to the method of the present invention yields neither of the results (P1), (P2), (M1), (M2) or (M3), the subject is determined to be highly likely not to suffer from PD or MSA, or to be likely to suffer from diseases other than PD or MSA. Specifically, this is the case where, when a biological sample from a subject is added to both of a solution containing the rod-like aggregate-producing monomers and a solution containing the twisted aggregate-producing monomers to simultaneously initiate aggregation reactions, no rapid amplification of α-synuclein aggregates is observed in either of the solutions, and rod-like aggregates are formed in the solution containing the rod-like aggregate-producing monomers, and twisted aggregates are formed in the solution containing twisted aggregate-producing monomers.

When the results other than (P1), (P2), (M1), (M2), or (M3) as described above are obtained for a subject who is suspected of suffering from PD or MSA, the subject is assumed to suffer from progressive supranuclear palsy, corticobasal degeneration, dystonia, spinocerebellar degeneration, or other diseases. The method of the present invention is thus very useful not only for providing early diagnosis of PD and MSA but also for contributing to early diagnosis of other diseases.

The aggregates can be quantified in step (4) of the method of the present invention as described above, and based on the quantification of the aggregates, the amount of the aggregates contained in the biological sample can be estimated. The present invention is therefore also suitable for determining the therapeutic effect of disease-modifying therapy for Parkinson's disease and/or multiple system atrophy.

Kit

The present invention provides a kit for performing the method of the present invention as described above. In other words, the kit of the present invention may be a kit for discriminating between PD and MSA, or a kit for supporting diagnosis of PD or MSA. The kit of the present invention may comprise a solution containing α-synuclein monomers having a tendency to produce rod-like aggregates or a solution containing α-synuclein monomers having a tendency to produce twisted aggregates; or may comprise both solutions. The α-synuclein monomers may be in any form, including a solution of the α-synuclein monomers in an appropriate buffer solution, or a lyophilized product of a solution of the α-synuclein monomers.

The components of the kit other than the α-synuclein monomers may include, but are not limited to, for example, reaction tubes and multi-well plates, plate seals, artificial fibrils (rod-like fibrils and twisted fibrils) for generation of a standard curve, instruction manuals, etc. The kit of the present invention allows for performing the method of the present invention in a rapid and convenient manner.

EXAMPLES

The present invention will be described in more detail below with reference to Examples, but the present invention is not limited thereto.

Example 1: Discrimination Between Parkinson's Disease and Multiple System Atrophy Utilizing Structural Polymorphism of Wild-Type α-Synuclein Monomers (1) Purification of α-Synuclein

*Escherichia coli* BL21(DE3) transfected with an expression vector encoding wild-type human α-synuclein (see Yagi, H et al., J. Biol. Chem. 280, 38609-38616 (2005)) was cultured in accordance with the conventional method. *E. coli* cells were disrupted, and α-synuclein was purified in accordance with the method described by Araki et al. (Araki, K et al., Sci Rep. 2016 Jul. 29; 6:30473. doi: 10.1038/srep30473). Specifically, lysozyme was added to the cells, and the mixture was ultrasonicated to disrupt the cell wall components. Streptomycin was then added to remove the nucleic acid components. The disrupted cells were heated at high temperature and then centrifuged to precipitate a large amount of contaminating proteins. The supernatant was further precipitated by addition of ammonium sulfate to purify α-synuclein. The α-synuclein was further purified by ion exchange chromatography. This wild-type human α-synuclein consists of the amino acid sequence of SEQ ID NO: 1.

(2) Separation of α-Synuclein Monomer Conformers with Different Elution Properties in Size-Exclusion Chromatography The purified α-synuclein prepared in the above section (1) was subjected to size-exclusion chromatography (SEC). SEC was performed on an AKTAexplorer 100 (GE Healthcare) chromatography system equipped with a Superdex 200 10/300 GL (GE Healthcare) column. An α-synuclein solution prepared in Tris buffered saline (150 mM NaCl, 50 mM Tris HCl, pH 7.4) was injected onto the column at a flow rate of 1.0 mL/min for SEC analysis.

Figure 1:
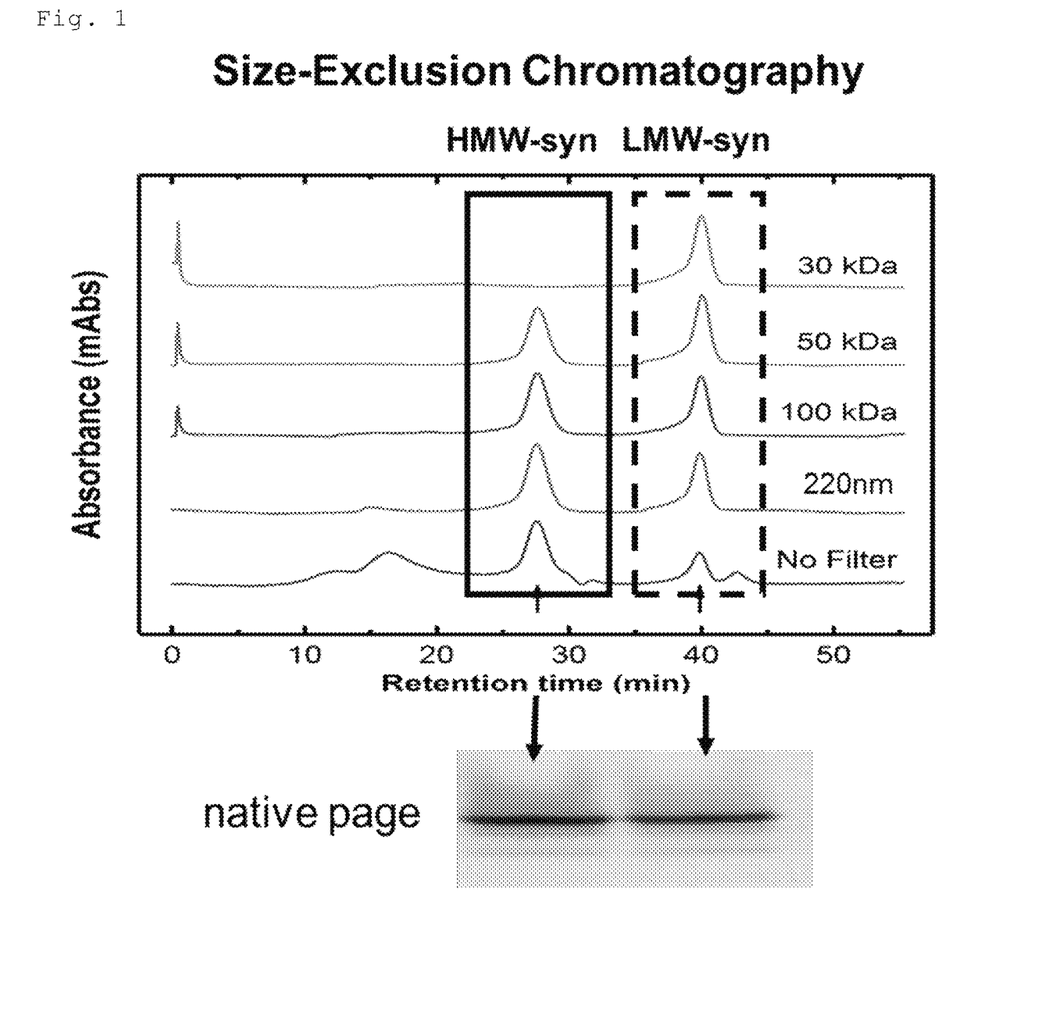

The results are shown in FIG. 1. The solution of the α-synuclein purified in the above section (1) directly subjected to SEC showed two peaks at retention times of about 28 and 40 minutes (FIG. 1, No Filter). Separation of the two peaks was then conducted by passing the solution through a sterilization filter (product name: Millex-GV, Millipore) and centrifugal ultrafiltration filter units (product name: Amicon Ultra, Millipore). A single peak was appeared in SEC at a retention time of about 28 minutes, indicating the presence of an α-synuclein monomer conformer, which was termed "HMW-syn." Another peak appeared at a retention time of about 40 minutes, indicating the presence of another α-synuclein monomer conformer, which was termed "LMW-syn."

As apparent from FIG. 1, SEC analysis of the solution that was passed through a 220 nm sterilization filter, a 100 kDa ultrafiltration filter or a 50 kDa ultrafiltration filter generated two peaks at the same retention times as those of the unfiltered solution (No Filter). However, SEC analysis of the solution passed through a 30 kDa ultrafiltration filter generated only a single peak at a retention time of about 40 minutes. These results indicate that the α-synuclein conformer with a peak at a retention time of about 28 minutes does not pass through the 30 kDa ultrafiltration filter. Native PAGE of the fractions of the peaks at retention times of about 28 and 40 minutes showed a single band at about 14 kDa, corresponding to the molecular weight of α-synuclein monomers.

(3) Formation of α-Synuclein Aggregates with Different Conformations

LMW-syn and HMW-syn were separated with a 30 kDa ultrafiltration filter. Then, a 0.5 mg/mL LMW-syn solution and a 0.5 mg/mL HMW-syn solution were prepared in Tris buffered saline (pH 7.4). ThT was added to the solutions to a final concentration of 10 μM, and the mixtures were ultrasonicated intermittently for 24 hours with alternating cycles of 1-minute ultrasonication and 9-minute resting. The reaction was performed at 37° C., and the fluorescence was measured with a fluorometer during every resting period. After 24 hours of ultrasonication, the formed aggregates were observed with a transmission electron microscope.

Figure 2:
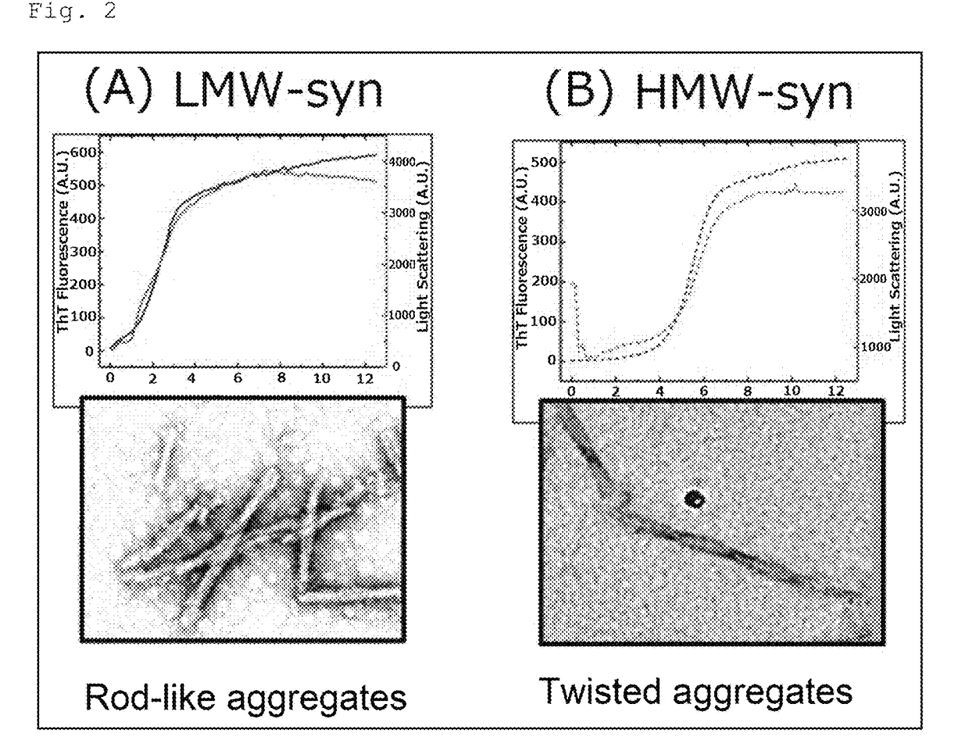

The results are shown in FIG. 2. (A) shows LMW-syn and (B) shows HMW-syn. The upper panels show the change of the fluorescence intensity over time, and the lower panels show images of the aggregates observed with a transmission electron microscope. Fluorescence intensity in the LMW-syn and HMW-syn solutions increased after intermittent ultrasonication, indicating amplification of aggregates. Aggregates of LMW-syn began to be amplified immediately after starting ultrasonication, whereas aggregates of HMW-syn began to be amplified about four hours after starting ultrasonication. Transmission electron microscope observations revealed that LMW-syn produces rod-like aggregates while HMW-syn produces twisted aggregates. Hereinafter, the rod-like aggregates formed from LMW-syn are called "aggregates A", and the twisted aggregates formed from HMW-syn are called "aggregates B."

(4) Investigation on Specificity of Cross-Seeding

Aggregates of prion-like proteins, including α-synuclein, are known to act as seeds for aggregate growth upon reaction with specific substrates (monomers). Based on this, the reaction products containing aggregates A or B were used as seeds to react with LMW-syn and HMW-syn to examine the specificity between the seeds and the substrates.

A 0.5 mg/mL LMW-syn solution and a 0.5 mg/mL HMW-syn solution were prepared in Tris buffered saline (pH 7.4). The seeds were added to the solutions to a final concentration of 5% (v/v), then ThT was added, and the mixtures were ultrasonicated intermittently for 24 hours with alternating cycles of 1-minute ultrasonication and 9-minute resting, in the same manner as in the above section (3). The reaction was performed at 37° C., and the fluorescence was measured with a fluorometer during every resting period. After 24 hours of ultrasonication, the formed aggregates were observed with a transmission electron microscope.

Figure 3:
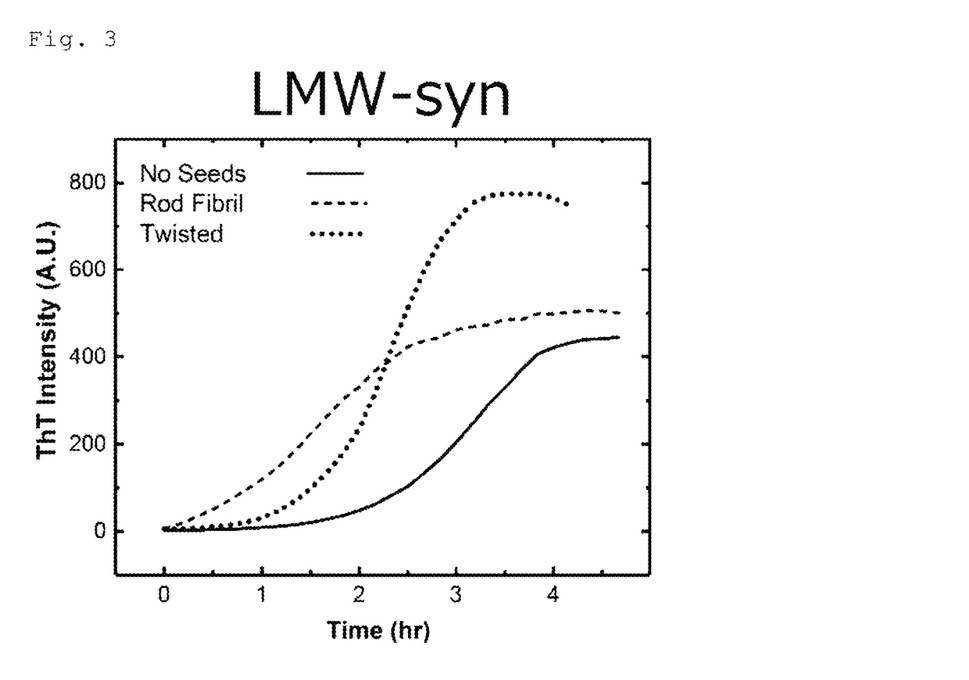
FIG. 3 is a graph of the fluorescence intensity measured over time in an LMW-syn solution after addition of rod-like aggregates or twisted aggregates of recombinant wild-type human α-synuclein as seeds and subsequent addition of ThT followed by intermittent ultrasonication (alternating cycles of 1-minute ultrasonication and 9-minute resting) for 24 hours.
Figure 4:
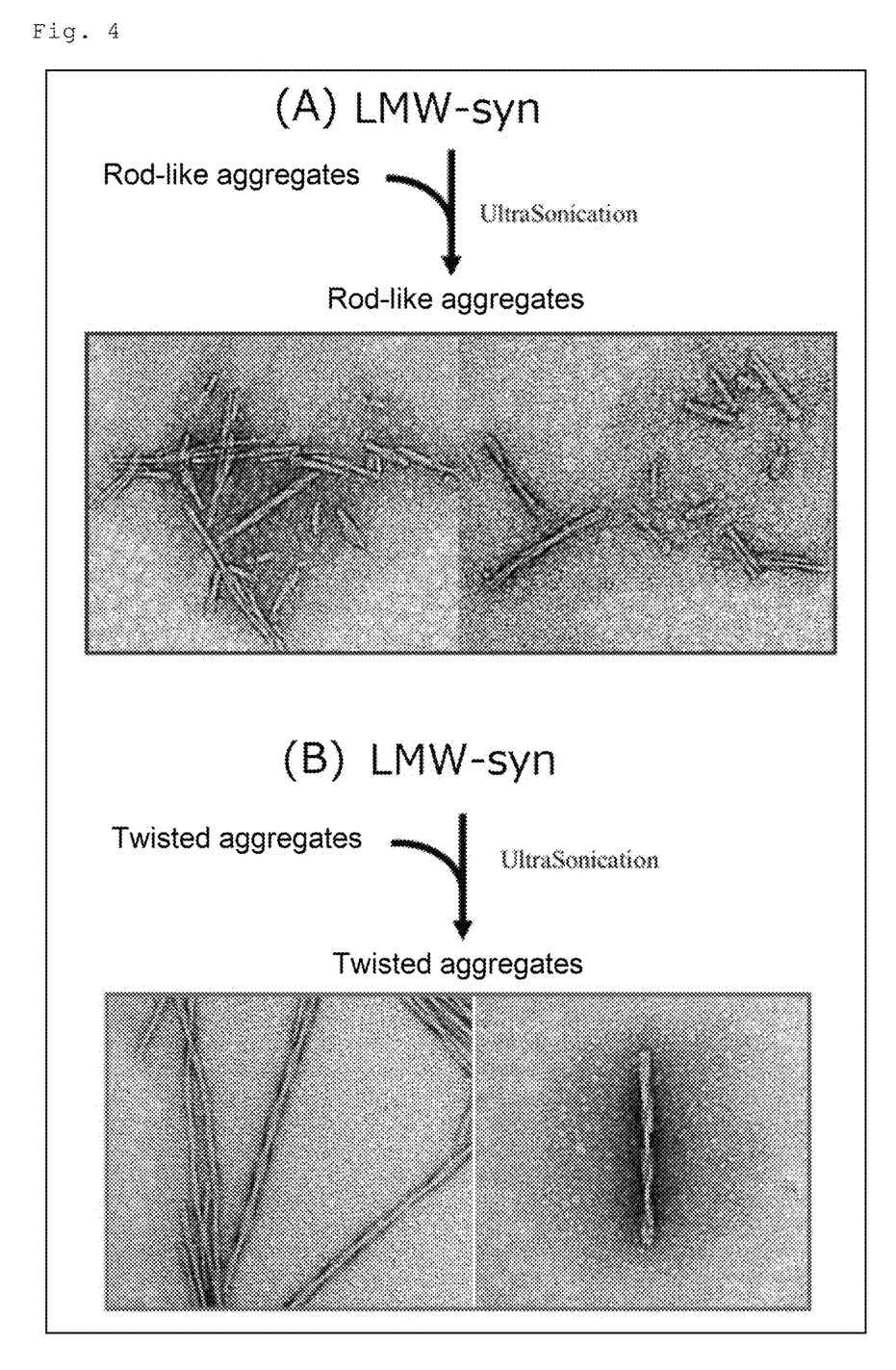
FIG. 4 shows transmission electron microscope images of aggregates formed after 24 hours of ultrasonication in the experiments shown in FIG. 3. (A) shows the images after addition of rod-like aggregates as seeds, and (B) shows the images after addition of twisted aggregates as seeds.

The results of the study using LMW-syn are shown in FIGS. 3 and 4. Addition of aggregates A as seeds to the LMW-syn solution resulted in rapid amplification of aggregates A, whereas addition of aggregates B as seeds to the LMW-syn solution resulted in rapid amplification of aggregates B. The results indicate that both of aggregates A and B have seeding effect on LMW-syn.

Figure 5:
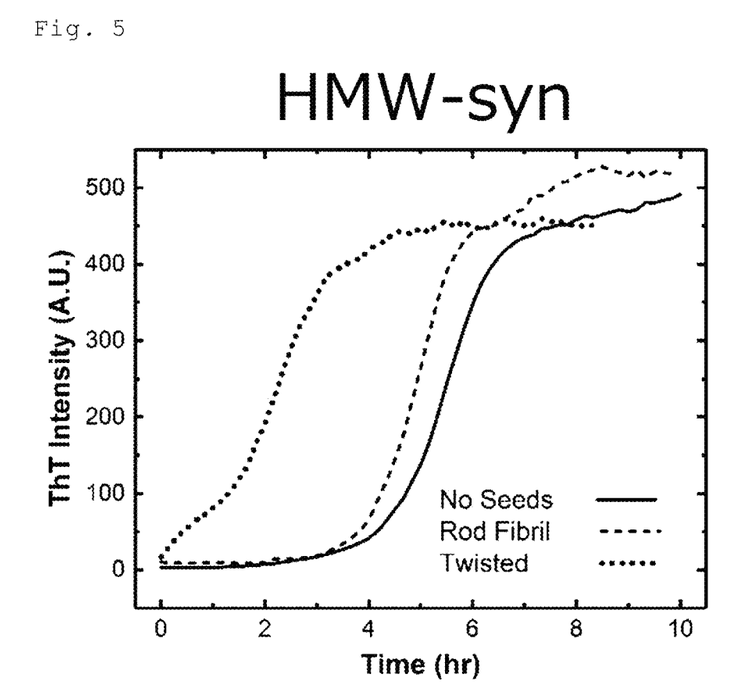
FIG. 5 is a graph of the emission fluorescence intensity measured over time in an HMW-syn solution after addition of rod-like aggregates or twisted aggregates of recombinant wild-type human α-synuclein as seeds and subsequent addition of ThT followed by intermittent ultrasonication (alternating cycles of 1-minute ultrasonication and 9-minute resting) for 24 hours.
Figure 6:
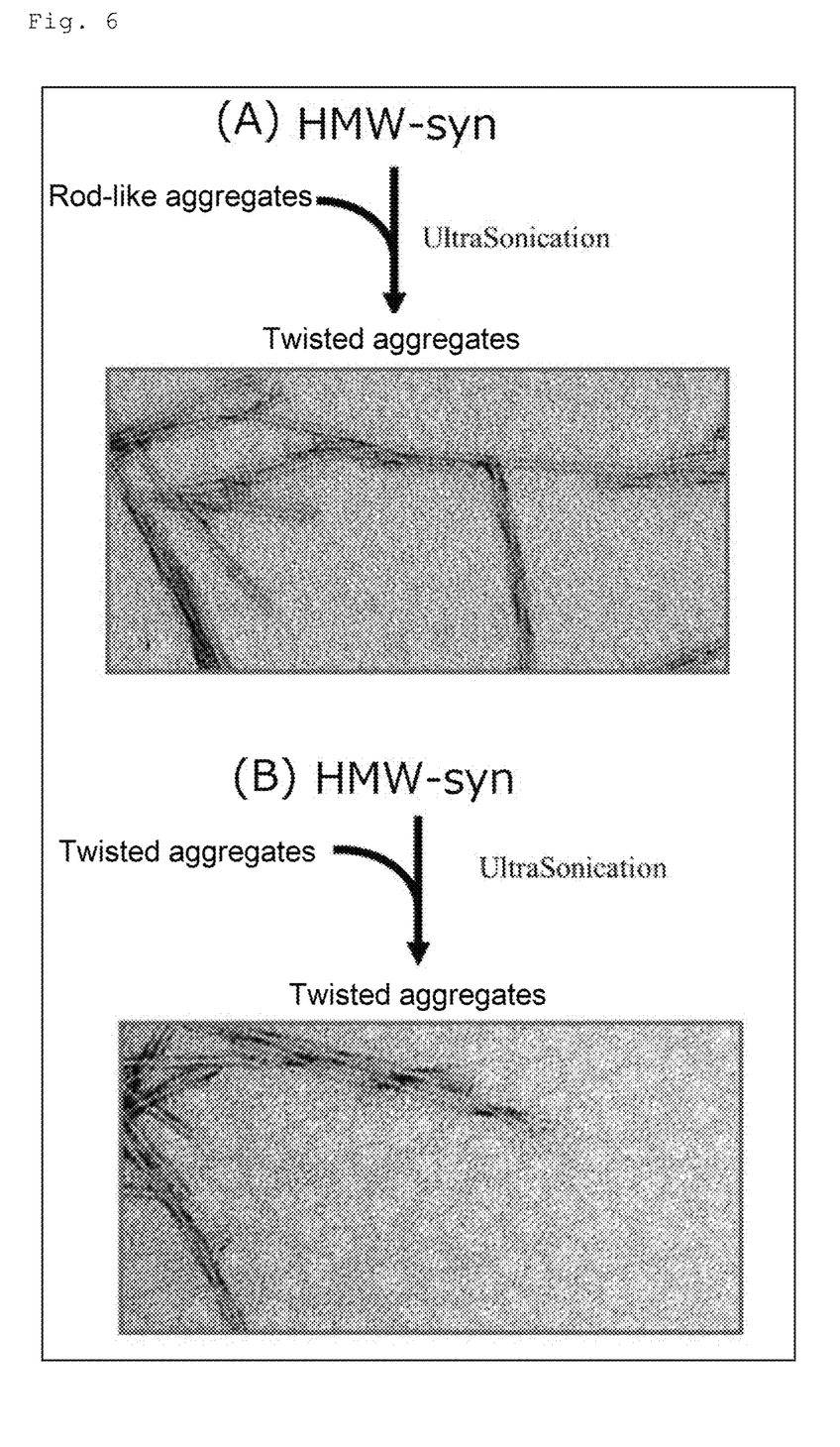
FIG. 6 shows transmission electron microscope images of aggregates formed after 24 hours of ultrasonication in the experiments shown in FIG. 5. (A) shows the image after addition of rod-like aggregates as seeds, and (B) shows the image after addition of twisted aggregates as seeds.

The results of the study using HMW-syn are shown in FIGS. and 6. No seeding effect (no rapid amplification of aggregates) was observed upon addition of aggregates A as seeds to the HMW-syn solution. The end products were aggregates B (twisted aggregates). However, addition of aggregates B as seeds resulted in rapid amplification of aggregates B, demonstrating that aggregates B have seeding effect on HMW-syn.

(5) Investigation Using Cerebrospinal Fluid from Patients

The cerebrospinal fluid was collected from patients with PD or MSA as well as patients with dystonia, which is a disease that does not feature accumulation of α-synuclein. The cerebrospinal fluid was added to an LMW-syn solution and an HMW-syn solution to investigate the presence or absence of seeding effect and the shape of the end products (aggregates).

Specifically, a 0.5 mg/mL LMW-syn solution and a 0.5 mg/mL HMW-syn solution were prepared in Tris buffered saline (pH 7.4). The cerebrospinal fluid from each patient was added to the solutions to a concentration of 5% (v/v), then ThT was added, and the mixtures were ultrasonicated intermittently for 24 hours with alternating cycles of 1-minute ultrasonication and 9-minute resting, in the same manner as in the above section (3). The reaction was performed at 37° C., and the fluorescence was measured with a fluorometer during every resting period. After 24 hours of ultrasonication, the formed aggregates were observed with a transmission electron microscope.

Figure 7:
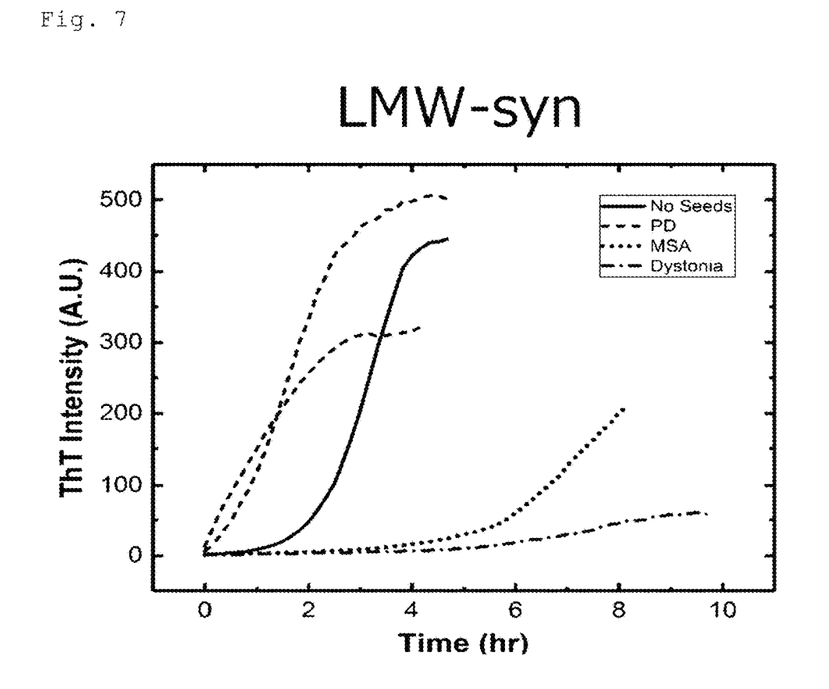
FIG. 7 is a graph of the emission fluorescence intensity measured over time in an LMW-syn solution after addition of the cerebrospinal fluid from patients with PD, MSA or dystonia as seeds and subsequent addition of ThT followed by intermittent ultrasonication (alternating cycles of 1-minute ultrasonication and 9-minute resting) for 24 hours.
Figure 8:
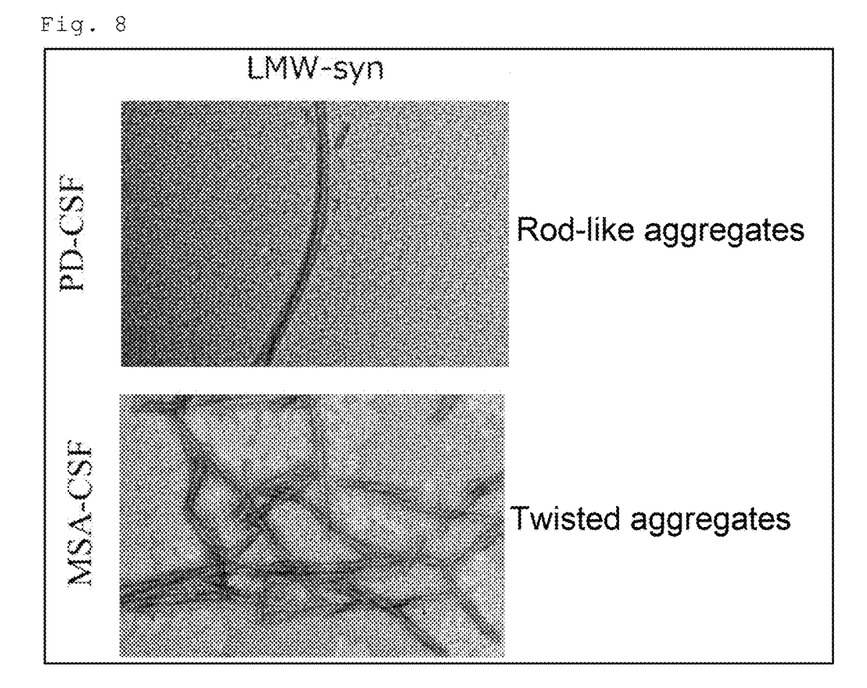
FIG. 8 shows transmission electron microscope images of aggregates formed at 24 hours after addition of the cerebrospinal fluid from patients with PD or MSA as seeds in the experiments shown in FIG. 7.

The results of the study using LMW-syn are shown in FIGS. and 8. Addition of the cerebrospinal fluid from the patients with PD to the LMW-syn solution resulted in rapid amplification of aggregates, and the end products were rod-like aggregates (aggregates A). However, no rapid amplification of aggregates was observed when the cerebrospinal fluid from the patients with MSA was added to the LMW-syn solution, and a longer reaction time was needed. The end products were twisted aggregates (aggregates B). The reaction with addition of the cerebrospinal fluid from the patients with dystonia was much slower than that with addition of the cerebrospinal fluid from the patients with MSA. The end products were rod-like aggregates (aggregates A).

Figure 9:
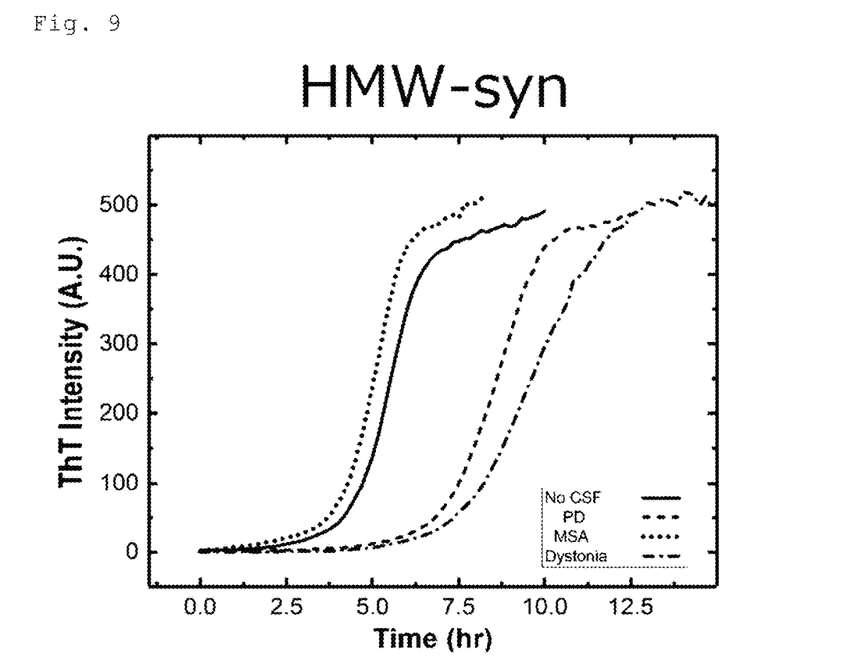
FIG. 9 is a graph of the emission fluorescence intensity measured over time in an HMW-syn solution after addition of the cerebrospinal fluid from patients with PD, MSA or dystonia as seeds and subsequent addition of ThT followed by intermittent ultrasonication (alternating cycles of 1-minute ultrasonication and 9-minute resting) for 24 hours.
Figure 10:
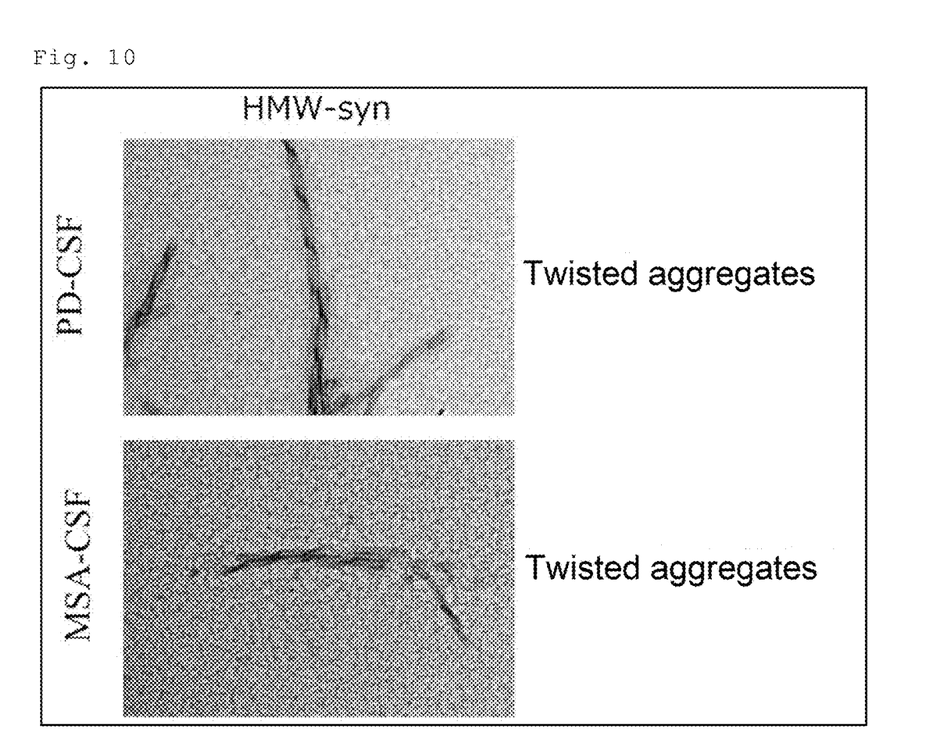
FIG. 10 shows transmission electron microscope images of aggregates formed at 24 hours after addition of the cerebrospinal fluid from patients with PD or MSA as seeds in the experiments shown in FIG. 9.

The results of the study using HMW-syn are shown in FIGS. 9 and 10. When the cerebrospinal fluid from the patients with MSA was added to the HMW-syn solution, amplification reaction of aggregates proceeded more rapidly than that with addition of the cerebrospinal fluid from the patients with PD. The reaction with addition of the cerebrospinal fluid from the patients with dystonia was much slower than that with addition of the cerebrospinal fluid from the patients with PD. The end products of the reactions with either cerebrospinal fluid were twisted aggregates (aggregates B).

The above results are summarized in the Table 1 below. The results demonstrate that Parkinson's disease and multiple system atrophy can be discriminated from each other.

TABLE 1

| Cerebrospinal fluid | α-synuclein monomers | Amplification reaction | Conformation of aggregates |
|---|---|---|---|
| Parkinson's disease | LMW-syn | Rapid | Rod-like |
|  | HMW-syn | Slow | Twisted |
| Multiple system atrophy | LMW-syn | Slow | Twisted |
|  | HMW-syn | Rapid | Twisted |
| Other diseases | LMW-syn | Slow | Rod-like |
|  | HMW-syn | Slow | Twisted |

The present invention is not limited to each of the embodiments and Examples as described above, and various modifications are possible within the scope of the claims. Embodiments obtainable by appropriately combining the technical means disclosed in the different embodiments of the present invention are also included in the technical scope of the present invention. The contents of the scientific literature and the patent literature cited herein are hereby incorporated by reference in their entirety.

The invention claimed is:

1. A method for discriminating between Parkinson's disease and multiple system atrophy, the method comprising:
   (1) preparing α-synuclein monomers by passing α-synuclein monomers through an ultrafiltration membrane filter with a molecular weight cut-off of 30 kDa to create a first fraction comprising α-synuclein monomers that pass through the ultrafiltration membrane filter which are capable of producing aggregates having a straight shape without twisting, as can be observed with a transmission electron microscope, and a second fraction comprising α-synuclein monomers that do not pass through the ultrafiltration membrane filter which are capable of producing aggregates having a twisted shape, as can be observed with a transmission electron microscope;
   (2) preparing a solution containing said first fraction of α-synuclein monomers, and/or a solution containing said second fraction of α-synuclein monomers,
   (3) adding a biological sample from a subject to the solution(s) containing the α-synuclein monomers prepared in step (2);
   (4) allowing the α-synuclein monomers to aggregate in the solution(s) obtained in step (3); and
   (5) detecting α-synuclein aggregates formed in step (3)(4) by enzyme immunoassay (EIA), immunochromatographic assay, latex agglutination method, radioimmunoassay (RIA), fluoroimmunoassay (FIA), luminescence immunoassay, surface plasmon resonance (SPR), Western blotting, electron microscopy, fluorescence microscopy, or fluorescence spectrometry,
   wherein after addition of the biological sample from the subject to the solution containing the first fraction of α-synuclein monomers, step (4) is initiated simultaneously both in the solution and in a control not containing the biological sample, and wherein when amplification of α-synuclein aggregates in the solution containing the biological sample is more rapid than that in the control, the subject is determined to suffer from Parkinson's disease, and
   wherein after addition of the biological sample from the subject to both the solution containing the first fraction of α-synuclein monomers, and the solution containing the second fraction of α-synuclein monomers, step (4) is initiated simultaneously in both solutions, and wherein when amplification of α-synuclein aggregates in the solution containing the first fraction of α-synuclein monomers, is more rapid than that in the solution containing the second fraction of α-synuclein monomers, the subject is determined to suffer from Parkinson's disease.

2. A method for supporting diagnosis of Parkinson's disease or multiple system atrophy, the method comprising:
   (1) preparing α-synuclein monomers by passing α-synuclein monomers through an ultrafiltration membrane filter with a molecular weight cut-off of 30 kDa to create a first fraction comprising α-synuclein monomers that pass through the ultrafiltration membrane filter which are capable of producing aggregates having a straight shape without twisting, as can be observed with a transmission electron microscope, and a second fraction comprising α-synuclein monomers that do not pass through the ultrafiltration membrane filter which are capable of producing aggregates having a twisted shape, as can be observed with a transmission electron microscope;

(2) preparing a solution containing said first fraction of α-synuclein monomers, and/or a solution containing said second fraction of α-synuclein monomers, (3) adding a biological sample from a subject to the solution(s) containing the α-synuclein monomers prepared in step (2);

(4) allowing the α-synuclein monomers to aggregate in the solution(s) obtained in step (3); and (3);

(5) detecting α-synuclein aggregates formed in step (3)(4) by enzyme immunoassay (EIA), immunochromatographic assay, latex agglutination method, radioimmunoassay (RIA), fluoroimmunoassay (FIA), luminescence immunoassay, surface plasmon resonance (SPR), Western blotting, electron microscopy, fluorescence microscopy, or fluorescence spectrometry, wherein after addition of the biological sample from the subject to the solution containing the first fraction of α-synuclein monomers, step (4) is initiated simultaneously both in the solution and in a control not containing the biological sample, and wherein when amplification of α-synuclein aggregates in the solution containing the biological sample is more rapid than that in the control, the subject is determined to suffer from Parkinson's disease, and wherein after addition of the biological sample from the subject to both the solution containing the first fraction of α-synuclein monomers, and the solution containing the second fraction of α-synuclein monomers, step (4) is initiated simultaneously in both solutions, and wherein when amplification of α-synuclein aggregates in the solution containing the first fraction of α-synuclein monomers, is more rapid than that in the solution containing the second fraction of α-synuclein monomers, the subject is determined to suffer from Parkinson's disease.

3. The method according to claim 1, wherein the α-synuclein consists of an amino acid sequence having 95% or more sequence identity to the amino acid sequence of SEQ ID NO: 1.

4. The method according to claim 1 or 2, wherein when the α-synuclein aggregates amplified after addition of the biological sample from the subject to the solution containing the α-synuclein monomers, which are capable of producing aggregates having a straight shape without twisting, are producing aggregates having a straight shape without twisting, the subject is determined to suffer from Parkinson's disease.

5. A method for discriminating between Parkinson's disease and multiple system atrophy, the method comprising:

(1) preparing α-synuclein monomers by passing α-synuclein monomers through an ultrafiltration membrane filter with a molecular weight cut-off of 30 kDa to create a first fraction comprising α-synuclein monomers that pass through the ultrafiltration membrane filter which are capable of producing aggregates having a straight shape without twisting, as can be observed with a transmission electron microscope, and a second fraction comprising α-synuclein monomers that do not pass through the ultrafiltration membrane filter which are capable of producing aggregates having a twisted shape, as can be observed with a transmission electron microscope;

(2) preparing a solution containing said first fraction of α-synuclein monomers, and/or a solution containing said second fraction of α-synuclein monomers, (3) adding a biological sample from a subject to the solution(s) containing the α-synuclein monomers prepared in step (2);

(4) allowing the α-synuclein monomers to aggregate in the solution(s) obtained in step (3); and (5) detecting α-synuclein aggregates formed in step (3)(4) by enzyme immunoassay (EIA), immunochromatographic assay, latex agglutination method, radioimmunoassay (RIA), fluoroimmunoassay (FIA), luminescence immunoassay, surface plasmon resonance (SPR), Western blotting, electron microscopy, fluorescence microscopy, or fluorescence spectrometry, wherein after addition of the biological sample from the subject to the solution containing the α-synuclein monomers, which are capable of producing aggregates having a twisted shape, step (4) is initiated simultaneously both in the solution and in a control not containing the biological sample, and wherein when amplification of α-synuclein aggregates in the solution containing the biological sample is more rapid than that in the control, the subject is determined to suffer from multiple system atrophy, wherein after addition of the biological sample from the subject simultaneously to both of the solution containing the α-synuclein monomers, which are capable of producing aggregates having a straight shape without twisting and the solution containing the α-synuclein monomers, which are capable of producing aggregates having a twisted shape, step (4) is initiated simultaneously in both solutions, and wherein when amplification of α-synuclein aggregates in the solution containing the α-synuclein monomers, which are capable of producing aggregates having a twisted shape is more rapid than that in the solution containing the α-synuclein monomers, which are capable of producing aggregates having a straight shape without twisting, the subject is determined to suffer from multiple system atrophy, wherein when both of the α-synuclein aggregates formed after addition of the biological sample from the subject to the solution containing the α-synuclein monomers, which are capable of producing aggregates having a straight shape without twisting and the α-synuclein aggregates formed after addition of the biological sample from the subject to the solution containing the α-synuclein monomers, which are capable of producing aggregates having a twisted shape are aggregates having a twisted shape of α-synuclein, the subject is determined to suffer from multiple system atrophy.

6. A method for supporting diagnosis of Parkinson's disease or multiple system atrophy, the method comprising:

(1) preparing α-synuclein monomers by passing α-synuclein monomers through an ultrafiltration membrane filter with a molecular weight cut-off of 30 kDa to create a first fraction comprising α-synuclein monomers that pass through the ultrafiltration membrane filter which are capable of producing aggregates having a straight shape without twisting, as can be observed with a transmission electron microscope, and a second fraction comprising α-synuclein monomers that do not pass through the ultrafiltration membrane filter which are capable of producing aggregates having a twisted shape, as can be observed with a transmission electron microscope;

(2) preparing a solution containing said first fraction of α-synuclein monomers, and/or a solution containing said second fraction of α-synuclein monomers, (3) adding a biological sample from a subject to the solution(s) containing the α-synuclein monomers prepared in step (2);

(4) allowing the α-synuclein monomers to aggregate in the solution(s) obtained in step (3); and (5) detecting α-synuclein aggregates formed in step (3)(4) by enzyme immunoassay (EIA), immunochromatographic assay, latex agglutination method, radioimmunoassay (RIA), fluoroimmunoassay (FIA), luminescence immunoassay, surface plasmon resonance (SPR), Western blotting, electron microscopy, fluorescence microscopy, or fluorescence spectrometry, wherein after addition of the biological sample from the subject to the solution containing the α-synuclein monomers, which are capable of producing aggregates having a twisted shape, step (4) is initiated simultaneously both in the solution and in a control not containing the biological sample, and wherein when amplification of α-synuclein aggregates in the solution containing the biological sample is more rapid than that in the control, the subject is determined to suffer from multiple system atrophy, wherein after addition of the biological sample from the subject simultaneously to both of the solution containing the α-synuclein monomers, which are capable of producing aggregates having a straight shape without twisting and the solution containing the α-synuclein monomers, which are capable of producing aggregates having a twisted shape, step (4) is initiated simultaneously in both solutions, and wherein when amplification of α-synuclein aggregates in the solution containing the α-synuclein monomers, which are capable of producing aggregates having a twisted shape is more rapid than that in the solution containing the α-synuclein monomers, which are capable of producing aggregates having a straight shape without twisting, the subject is determined to suffer from multiple system atrophy, wherein when both of the α-synuclein aggregates formed after addition of the biological sample from the subject to the solution containing the α-synuclein monomers, which are capable of producing aggregates having a straight shape without twisting and the α-synuclein aggregates formed after addition of the biological sample from the subject to the solution containing the α-synuclein monomers, which are capable of producing aggregates having a twisted shape are aggregates having a twisted shape of α-synuclein, the subject is determined to suffer from multiple system atrophy.

* * * * *

SEQUENCE LISTING

```
<160> NUMBER OF SEQ ID NOS: 4

<210> SEQ ID NO 1
<211> LENGTH: 140
<212> TYPE: PRT
<213> ORGANISM: Homo sapiens

<400> SEQUENCE: 1

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
```

```
                50                  55                  60
Asn Val Gly Gly Ala Val Val Thr Gly Val Thr Ala Val Ala Gln Lys
 65                  70                  75                  80

Thr Val Glu Gly Ala Gly Ser Ile Ala Ala Thr Gly Phe Val Lys
                 85                  90                  95

Lys Asp Gln Leu Gly Lys Asn Glu Glu Gly Ala Pro Gln Glu Gly Ile
                100                 105                 110

Leu Glu Asp Met Pro Val Asp Pro Asp Asn Glu Ala Tyr Glu Met Pro
            115                 120                 125

Ser Glu Glu Gly Tyr Gln Asp Tyr Glu Pro Glu Ala
            130                 135                 140

<210> SEQ ID NO 2
<211> LENGTH: 140
<212> TYPE: PRT
<213> ORGANISM: Mus musculus

<400> SEQUENCE: 2

Met Asp Val Phe Met Lys Gly Leu Ser Lys Ala Lys Glu Gly Val Val
  1               5                  10                  15

Ala Ala Ala Glu Lys Thr Lys Gln Gly Val Ala Glu Ala Ala Gly Lys
                 20                  25                  30

Thr Lys Glu Gly Val Leu Tyr Val Gly Ser Lys Thr Lys Glu Gly Val
             35                  40                  45

Val His Gly Val Thr Thr Val Ala Glu Lys Thr Lys Glu Gln Val Thr
 50                  55                  60

Asn Val Gly Gly Ala Val Val Thr Gly Val Thr Ala Val Ala Gln Lys
 65                  70                  75                  80

Thr Val Glu Gly Ala Gly Asn Ile Ala Ala Ala Thr Gly Phe Val Lys
                 85                  90                  95

Lys Asp Gln Met Gly Lys Gly Glu Glu Gly Tyr Pro Gln Glu Gly Ile
                100                 105                 110

Leu Glu Asp Met Pro Val Asp Pro Gly Ser Glu Ala Tyr Glu Met Pro
            115                 120                 125

Ser Glu Glu Gly Tyr Gln Asp Tyr Glu Pro Glu Ala
            130                 135                 140

<210> SEQ ID NO 3
<211> LENGTH: 140
<212> TYPE: PRT
<213> ORGANISM: Rattus norvegicus

<400> SEQUENCE: 3

Met Asp Val Phe Met Lys Gly Leu Ser Lys Ala Lys Glu Gly Val Val
  1               5                  10                  15

Ala Ala Ala Glu Lys Thr Lys Gln Gly Val Ala Glu Ala Ala Gly Lys
                 20                  25                  30

Thr Lys Glu Gly Val Leu Tyr Val Gly Ser Lys Thr Lys Glu Gly Val
             35                  40                  45

Val His Gly Val Thr Thr Val Ala Glu Lys Thr Lys Glu Gln Val Thr
 50                  55                  60

Asn Val Gly Gly Ala Val Val Thr Gly Val Thr Ala Val Ala Gln Lys
 65                  70                  75                  80

Thr Val Glu Gly Ala Gly Asn Ile Ala Ala Ala Thr Gly Phe Val Lys
                 85                  90                  95

Lys Asp Gln Met Gly Lys Gly Glu Glu Gly Tyr Pro Gln Glu Gly Ile
```

```
                100             105             110
Leu Glu Asp Met Pro Val Asp Pro Ser Ser Glu Ala Tyr Glu Met Pro
            115                 120                 125

Ser Glu Glu Gly Tyr Gln Asp Tyr Glu Pro Glu Ala
            130                 135             140

<210> SEQ ID NO 4
<211> LENGTH: 140
<212> TYPE: PRT
<213> ORGANISM: Callithrix jacchus

<400> SEQUENCE: 4

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
            35                  40                  45

Val His Gly Val Thr Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Asn Ile Ala Ala Ala Thr Gly Phe Val Lys
            85                  90                  95

Lys Asp His Leu Gly Lys Ser Glu Glu Gly Ala Pro Gln Glu Gly Ile
            100                 105                 110

Leu Glu Asp Met Pro Val Asp Pro Asp Asn Glu Ala Tyr Glu Met Pro
            115                 120                 125

Ser Glu Glu Gly Tyr Gln Asp Tyr Glu Pro Glu Ala
            130                 135             140
```